United States Patent [19]
Tisdale et al.

[11] Patent Number: 6,103,246
[45] Date of Patent: Aug. 15, 2000

[54] CREAMS AND LOTIONS CONTAINING EMU OIL

[76] Inventors: Carrie J. Tisdale, Rte. 8 Box 47D4, Lubbock, Tex. 79416; Alexander Zemtsov, #3 Stirrup La., Ransom Canyon, Tex. 79366

[21] Appl. No.: 09/027,419

[22] Filed: Feb. 23, 1998

Related U.S. Application Data

[63] Continuation of application No. 08/751,448, Nov. 1, 1996, abandoned, which is a continuation of application No. 08/590,801, Jan. 24, 1996, abandoned, which is a continuation of application No. 08/411,069, Mar. 27, 1995, abandoned, which is a continuation of application No. 08/071,711, Jun. 3, 1993, abandoned.

[51] Int. Cl.$^7$ ..................................................... A61K 7/48
[52] U.S. Cl. .......................... 424/401; 424/450; 514/557; 514/844; 514/846; 514/938; 514/937
[58] Field of Search ..................................... 424/401, 450; 514/557, 844, 846, 937, 938

[56] References Cited

U.S. PATENT DOCUMENTS 4,234,599  11/1980  Van Scott et al. ...................... 424/279

OTHER PUBLICATIONS

"Emu–Natural Emu Oil" Brochure by Emu vertica of PERTH, Western Australia, Sep. 1992.

"Your Guide To Natural Beauty Products" By Jane Heimlich, Dr. Julian Whitaker's Health and healing, Mar. 1993.

*Primary Examiner*—Jyothsna Venkat
*Attorney, Agent, or Firm*—Akin, Gump, Strauss, Hauer & Feld, L.L.P.

[57] ABSTRACT

A composition which is a cream or lotion for topical application to human skin. The composition includes emu oil as a component. Emu oil is generally comprised of myristic acid, palmitic acid, palmitoleic acid, margaric acid, stearic acid, elaidic acid, oleic acid, vaccenic acid, linoleic acid, linolenic acid, arachidic acid and eicosenoic acid. The composition also includes a medically active component, such as lactic acid or some other alpha-hydroxy acid. The balance of the components of the composition are water, glycerin, and an emulsion base. Liposomes may be included in the composition. The composition provides for increased skin penetrability due to the emu oil.

7 Claims, No Drawings

CREAMS AND LOTIONS CONTAINING EMU OIL

The present application is a continuation of Ser. No. 08/751,448 Nov. 1, 1996, now abandoned; which is a continuation of Ser. No. 08/590,801 filed Jan. 24, 1996, now abandoned; which is a continuation of Ser. No. 08/411,069 filed Mar. 27, 1995, now abandoned; which is a continuation of Ser. No. 08/071,711 filed Jun. 3, 1993, now abandoned.

BACKGROUND OF THE INVENTION

1. Field of the Invention

The invention relates to creams and lotions suitable for application to the human skin, and, more particularly, to such creams and lotions containing, at least in part, oil derived from the emu bird.

2. Description of the Related Art

An emu is a large, flightless Australian bird, *Dromiceius novaehollandiae,* which is related to and resembles the ostrich. The emu is a member of the Ratite family of birds. The emu is the only bird of the Ratite family that has a subcutaneous layer of fat found just under the skin on the back of the bird. Other birds in that family have particular areas of body fat, but not a significant subcutaneous fat layer along the back as in the emu.

Within the last several years, it has become popular to raise and breed emus for commercial purposes. Emus can be commercially valuable livestock in several respects. For example, the meat of the emu may be eaten. That meat is a red meat, like beef from cattle. Emu meat is low in calories, low in cholesterol, high in protein, and high in iron. Further, the skin of the emu can be used as leather. The leather is a high quality, durable leather. It is thin like pigskin and so may be used in much the same manners as pigskin, such as for garments like women's clothing, skirts, jackets, vests, wallets, and boots, and for a multitude of other matters which may be made from leather. Even further, the feathers of the emu may be used in a number of ways. Emu feathers have been used for making fishing lures and in ornamental-type items, for example, jewelry.

Only recently has it become apparent that oil from the emu may have commercial value. Emu oil, in one form or another, has been used for many years by the Aborigines of Australia. The Aborigines have, in particular, used the oil to protect human skin from the adverse elements encountered in the Australian outback. The Aboriginal people have also used emu oil and fat for the treatment of arthritis and rheumatism. In certain of these applications, the Aborigines mix the emu oil with various other oils, for example, cineole or eucalyptus oil. Early explorers and bushmen have also extolled the merits of emu oil as an embrocation for relief of a number of ailments, including rheumatism, lumbago and joint stiffness.

Only recently has white settlement recognized and researched the therapeutic effects of emu oil. Combinations of emu oil and a suitable transdermal transporter have, in various tests, been demonstrated to exhibit anti-inflammatory activity, in the cases of inflammatory arthritis and similar joint swelling diseases. Ghosh, P. and Whitehouse, M., *Experimental Study to Determine the Anti-Arthritic Activity of a New Emu Oil Formulation (EMMP),* Ostrich Marketplace (Dec. 3, 1992). In those tests, it was found that emu oil exhibits certain surface penetrating characteristics that, when the oil is combined with other compounds, increases the penetration of the composition as a whole. There was indication in those studies that the compositions created some skin irritation. The use of emu oil has, thus, heretofore been considered effective only in combination with anti-inflammatory type compounds in which skin irritation is of less concern than penetrability.

Animal oils in general have not been used in traditional cosmetic formulations because those oils tend to be comedonic or otherwise irritable to the human skin. It has been known, however, that animal oils, due to their particular phospholipid concentrations, which are similar to that of the human skin, have penetration qualities. Nevertheless, though animal oils could have some beneficial penetration characteristics, animal oils have not generally been used in cosmetic creams and lotions because of the undesirable skin irritation consequences.

Various compounds in creams and lotions are presently recognized as medically active and beneficial when applied to the human skin. Certain of these compounds which have received considerable attention as of late include alpha-hydroxy acids. Alpha-hydroxy acids are commonly known as "fruit acids," because most are derived from apples, citrus, and grapes. The family of alpha-hydroxy acids includes a number of compounds, including, for example, lactic acid and glycolic acid. Alpha-hydroxy acids have certain desirable moisturizing characteristics and so have been used in various cosmetic compositions. Alpha-hydroxy acids act as moisturizers by loosening dead skin cells from the skin surface. They have much the same effect as a rough cloth or sponge that rubs off surface skin cells to uncover fresher cells. In technical terms, these acids reduce the thickness of hyperkeratotic stratum corneum by reducing corneocyte cohesion at lower levels of the skin stratum corneum. This property permits efficient clinical control of dry skin, ichthyosis, follicular hyper-keratosis, and other conditions characterized by retention of stratum corneum. Van Scott, E. J., and Yu, R. J., *Alpha-Hydroxy Acids: Procedures for Use in Clinical Practice,* Cutis (March 1989).

In addition to the alpha-hydroxy acids, a multitude of other substances, because of their desirable moisturizing characteristics, are used in cosmetic compositions. A substance being used only fairly recently in cosmetics is liposomes. Liposomes are microscopic bubbles formed of a lipid shell which encapsulate a portion of the solution in which the liposome is found. Liposomes may be manufactured and filled with a variety of medications. The capsule shell of liposomes may be similar in composition to the body's own skin oil. Therefore, liposomes can serve to penetrate into the deep underlying layers of the skin where they then deliver their active moisturizing agents in a time-release action. Topical use of liposome drugs have been described in the literature. Korting, H.C., Blecher, P., Schafer-Korting, M., and Wendel, A., *Topical Liposomes to Come, What the Patent Literature Tells Us,* Journal of the American Academy of Dermatology (December 1991). Though liposomes have been observed to be somewhat effective when used in topical cosmetic applications due to their skin penetrating characteristics, the major focus for use of liposomes in the past has been with topical inflammatory agents, in particular, corticosteroids.

Even liposomes have proven only partially effective in providing adequate penetrability, as desired for many cosmetics applications. Further, the addition of liposomes to cosmetics preparations can significantly increase the cost of the preparations. Clearly, it would be both technologically and commercially advantageous to use some other or additional penetrating composition in cosmetics to achieve desired penetration results. The present invention provides a significantly improved cosmetic compound, effective in providing desired penetration in human skin and, yet, maintaining appropriate effectiveness of the compound as a whole, without adverse consequences to the user or otherwise. Further, the present invention is more cost-effective than many of the penetrating compounds heretofore employed. The present invention is thus a significant improvement in the art.

SUMMARY OF THE INVENTION

In one embodiment, the invention is a composition for topical application to human skin. The invention comprises emu oil and at least one medically active compound.

In another aspect, the emu oil is about 1 weight percent to about 10 weight percent of the composition.

In a further aspect, at least one medically active compound is an alpha-hydroxy acid.

In an even further aspect, the invention further comprises water, and glycerin.

In yet another aspect, the invention further comprises an emulsion selected from a group consisting of water/oil emulsion and oil/water emulsion.

In even another aspect, the invention further comprises liposomes.

In a further aspect, the alpha-hydroxy acid is selected from a group consisting of lactic acid, glycolic acid, and pyruvic acid.

In an even further aspect, the alpha-hydroxy acid is about 0 weight percent to about 20 weight percent of the composition.

In yet another further aspect, the emu oil is about 4.2 weight percent, at least one medically active compound is about 3 weight percent to about 6 weight percent, the water is about 9.5 weight percent to about 25 weight percent, and the glycerin is about 2 weight percent to about 9.5 weight percent of the composition.

In another aspect, the invention comprises an emulsion base.

In another embodiment, the invention a lotion for topical application to the human skin having the improvement comprising emu oil in the lotion.

In yet another embodiment, the invention is a composition, comprised of myristic acid, palmitic acid, palmitoleic acid, margaric acid, stearic acid, elaidic acid, oleic acid, vaccenic acid, linoleic acid, linolenic acid, arachidic acid, eicosenoic acid, and as least one medically active component.

In a further aspect, the composition is for topical application to human skin.

In an even further aspect, the invention further comprises water, glycerin, and an emulsion base.

In yet another aspect, the medically active compound is an alpha-hydroxy acid

In yet another embodiment, the invention is a method for making a composition for topical application to human skin. The invention comprises the steps of processing an emu to obtain a subcutaneous fat layer from the emu, rendering the subcutaneous fat layer to obtain an oil, and combining the oil with at least one medically active compound.

In another aspect, the rendering step is performed as a cold rendering process.

In further aspect, at least one medically active compound is an alpha-hydroxy acid.

In yet another aspect, the oil is about 1 weight percent to about 10 weight percent of the composition.

In yet a further aspect, the invention further comprises the steps of adding water to the composition, adding glycerin to the composition, and adding an emulsion base to the composition.

DETAILED DESCRIPTION OF THE INVENTION

The following detailed description primarily addresses a preferred embodiment of the present invention. Those skilled in the art will readily recognize, however, that the invention may be satisfactorily employed in other applications and that alternative aspects and embodiments of the invention are possible. All those other applications, aspects, and embodiments of the invention are hereby expressly included in, and form a part of, the invention.

Emu oil is obtained from the emu bird. The emu bird has a subcutaneous layer of fat extending along the back of the bird. The bird is processed by typical livestock processing means. Special care is taken in processing the bird in order to preserve and remove from the bird the subcutaneous layer of fat.

Once the subcutaneous layer of fat is removed from the emu bird, the layer of fat is processed to obtain emu oil. A cold rendering process is preferably employed to reduce the fat to oil. In this cold rendering process, the fat is melted down and then pressurized. Thereafter, a vectored wind is blown across the melted fat. This simultaneous pressuring and wind cooling removes impurities. The preferred process of rendering employed to obtain emu oil is termed "cold" herein because, during the melting step, the temperature is not raised so high as to winterize the oil. In a winterizing process, temperature of the fat is raised high to melt the fat and cause impurities to escape. The temperature is then quickly reduced to maintain the melted fat, now oil, free of impurities. Winterizing would not be appropriate for rendering emu oil for use in the invention because that process would make the emu oil very unstable. Therefore, it has been found that the "cold" rendering process, in which the temperature level is limited and in which a vectored wind is forced across the pressurized oil to remove impurities, is particularly effective in the processing of emu oil.

Emu oil has been observed to comprise substantially the following fatty acid components:

TABLE 1

COMPOSITION OF EMU OIL

| Component | Percent Composition* |
| --- | --- |
| Myristic Acid | 0.3 |
| Palmitic Acid | 17.5 |
| Stearic Acid | 10.1 |
| Arachidic Acid | 0.6 |
| Tetradecenoic Acid | 0.9 |
| Hexadecanoic Acid | 2.1 |
| Oleic Acid | 62.2 |
| Octadecadienoic Acid | 5.2 |
| Unsaturated $C_{20-22}$ Acids | 0.5 |

*Percent of Total Fatty Acids by weight Hil Ditch, T. P., The Chemical Composition of Natural Fats 2nd Ed. (John Wiley & Sons, Inc., 1949).

Of course, the composition of emu oil may vary according to a variety of matters, including, for example, the particular rendering process employed, types of storage containers, age and handling of the oil, environmental conditions in which the subject emu is found, distinctive characteristics of a particular animal, diet of the emu, and numerous other factors. It is, nevertheless, believed that most typical emu oil will, within a somewhat limited range, have approximately the composition listed above. It is of interest that, except for relatively low palmitic acid and high oleic acid contents, the body fat of the emu is similar to that of many larger land mammals.

The preferred emu oil for use in the present invention is obtained from Emu Vertica, a company having an address at 4/220 St. Georges Tce., Perth 6000, Western Australia. That particular emu oil has Australian Register Therapeutic Goods, Registration Number 22759. One analysis of that particular emu oil has yielded the following results:

| Fatty Acid | Percent of Total Fatty Acids* |
|---|---|
| Myristic | 0.3 |
| Palmitic | 21.0 |
| Palmitoleic | 3.2 |
| Margaric | 0.1 |
| Stearic | 9.1 |
| Elaidic | 0.3 |
| Oleic | 48.8 |
| Vaccenic | 2.0 |
| Linoleic | 12.8 |
| Linolenic | 1.1 |
| Arachidic | 0.1 |
| Eicosenoic | 0.4 |
| Unknown | 0.5 |

Although this particular emu oil is preferred, it is believed that any other emu oil, obtained from cold or any other processing means, and having any other similar composition, is substantially equally effective for purposes of the invention.

After the emu fat has been processed to obtain the emu oil, the emu oil is combined with other compounds, for example, medically active compounds. Medically active compounds include a wide variety of compounds which are active in inducing certain medical effects which are beneficial or otherwise therapeutic. For example, the emu oil can be combined with an alpha-hydroxy acid to obtain a cream or lotion for application to human skin. As previously mentioned, alpha-hydroxy acids include a number of naturally occurring acids, such as, lactic acid, glycolic acid, pyruvic acid, and others. Of the alpha-hydroxy acids, lactic acid, for instance, is known to have certain medical dermatological properties. In fact, any preparation comprised of in excess of 12% lactic acid must, in the United States, be prescribed by a medical doctor for use by a consumer. It is believed that certain others of the alpha-hydroxy acids are also medically beneficial topical products.

In a preferred embodiment of the present invention, emu oil and lactic acid are combined to form a cream or lotion for topical use by a human on the human skin. Such a cream or lotion may be used as a facial or hand cream or lotion, or may be used on other skin areas of the human body. In this preferred embodiment, certain other compounds are preferentially combined with the lactic acid and emu oil to give the cream or lotion desired solution and viscosity characteristics. Those compounds include water and glycerin which serve to vary the consistency and spreadability of the composition. An appropriate base compound, for example, Dermabase®, a water-oil emulsion commonly used in cosmetics, creams and oils to give desired thickness qualities, is also combined as part of the preferred composition. This combination of components i.e., emu oil, lactic acid, water, glycerin, and Dermabase®, provides a cream which is effective to penetrate the skin without resulting comedonic or allergenic side effects. The emu oil of the composition is believed to provide both penetrating and moisturizing benefits in application.

In the preferred embodiment, composition of the cream is as follows for facial cream and hand/body cream, respectively:

TABLE 2

COMPOSITION OF THE PREFERRED EMBODIMENT

| Component | Facial Cream* | Hand/Body Cream* |
|---|---|---|
| Lactic Acid | 3% | 6% |
| Emu Oil | 4.2% | 4.2% |
| Water | 25% | 9.5% |
| Glycerin | 2% | 9.5% |

*in quantity sufficient Dermabase ®

As previously briefly mentioned, Dermabase® is a well known base substance for use in cosmetics, creams and lotions. Those familiar with cosmetic, cream and lotion products for topical use by humans will recognize the particular product identified herein as Dermabase® and will readily know appropriate amounts of Dermabase® to be included in the composition in particular applications.

The above preferred composition of the invention has been subject to testing by Dr. Alexander Zemtsov, M.D., of the Texas Tech University Health Science Center. In the tests, all participants indicated that this preferred composition facilitates penetration through the skin when topically applied, but does not create adverse effects or exacerbate problem conditions. There is some evidence, in fact, that the preferred composition may have other or additional medical beneficial and therapeutic effects in certain applications.

In addition to the preferred composition for the present invention described above, a multitude of variations are possible for the composition and ingredients thereof. In alpha-hydroxy acid compositions of the present invention, the invention is effective when the composition contains approximately 1–10% emu oil and approximately 0–20% alpha-hydroxy acid. Further, however, different concentrations of emu oil and alpha-hydroxy acid may be appropriate in particular applications of the invention.

In any case, the remaining portion of the composition which is not emu oil or some active compound can be a neutral oil/water or water/oil emulsion ranging in an amount from approximately 70–98% of the total of the composition. It should be understood, however, that other concentrations of such an emulsion compound may be appropriate in particular instances. Dermabase® is a preferred oil/water emulsion for use in the composition. The glycerin and water of the composition serve merely to provide for suitable characteristics of the invention composition. Those skilled in the art will readily understand and appreciate that the desired concentration of these components of the compound may vary widely depending on the desired characteristics for the particular application.

In addition to lactic acid employed in the preferred composition, other alpha-hydroxy acids may be supplemented for, or added also with, the lactic acid. For example, glycolic acid and pyruvic acid may also be included in the composition in certain applications. The particular properties of glycolic acid and/or pyruvic acid must be considered for those applications; however, those skilled in the art will readily appreciate the appropriateness or inappropriateness of including those compounds in the composition in any instance. Other alpha-hydroxy acids, as well as numerous other compositions and ingredients, could additionally or alternatively be included in the compound. All of those various alpha-hydroxy acids and other compositions and ingredients combined with emu oil in accordance herewith are included in and form part of the invention.

Recently, much attention has been focused on the use of liposomes in cosmetics and other topical creams and lotions for the human skin. As previously mentioned, liposomes are microscopic balls made of a fatty compound, a lipid, which encapsulate droplets of a water-based emollient within the ball. Liposomes are particularly susceptible to use in topical skin compounds because when a liposome is rubbed into the skin, it releases the emollient throughout the stratum corneum of the skin. Use of liposomes in combination with emu oil may provide many of the same and even additional benefits observed by use of emu oil in the preferred composition and other compositions. Those skilled in the art will recognize appropriate liposomes to be employed in particular instances, and the compositions and variations thereof which may be appropriate. In any event, emu oil in any such application serves similar functions of increasing skin penetrability and moisturizing skin, without adverse effects.

In addition to those combinations described above, emu oil may be combined with a multitude of other ingredients and compounds in substantially the same manner as previously described. In each of those instances, the emu oil is expected to serve substantially the same function, i.e., increased penetrability and moisturizing without adverse effects, as for the particular compositions described herein. Therefore, each of those other compositions is expressly included herein and forms the invention.

As is clearly seen, the present invention overcomes the problems presented by the prior cosmetics and topical creams and lotions. The present invention is believed to be especially effective when composed and employed as described herein, however, those skilled in the art will readily recognize that numerous variations and substitutions may be made in the invention and its use and composition to achieve substantially the same results achieved by the embodiments and, in particular, the preferred embodiment, expressly described herein. Each of those variations is intended to be included in the description herein and forms a part of the present invention. The foregoing detailed description is, thus, to be clearly understood as being given by way of illustration and example only, the spirit and scope of the present invention being limited solely by the appended claims.

What is claimed is:

1. A composition for topical application to human skin, comprising:

emu oil; and at least one medically active compound wherein said medically active compound is selected from the group consisting of lactic acid, glycolic acid, and pyruvic acid, and wherein said emu oil is about 4.2 weight percent, said at least one medically active compound is about 3 weight percent to about 6 weight percent, said water is about 9.5 weight percent to about 25 weight percent, said glycerin is about 2 weight percent to about 9.5 weight percent of said composition.

2. The composition of claim 1, further comprising an emulsion selected from a group consisting of water/oil emulsion and oil/water emulsion.

3. The composition of claim 1, further comprising liposomes.

4. The composition of claim 1, further comprising an emulsion base.

5. A method for making a composition according to claim 1, for topical application to human skin, comprising the steps of:

processing an emu to obtain a subcutaneous fat layer from said emu;

rendering said subcutaneous fat layer to obtain an oil; and combining said oil with at least one medically active compound and adding water to said composition and adding glycerin to said composition.

6. The method of claim 5, wherein said rendering step is performed as a cold rendering process.

7. The method of claim 5, further comprising:

adding an emulsion base to said composition.

\* \* \* \* \*